United States Patent [19]

Ravo

[11] Patent Number: 4,719,916
[45] Date of Patent: Jan. 19, 1988

[54] INTRAINTESTINAL BYPASS TUBE

[76] Inventor: Biagio Ravo, Nassau Hospital, 259 First St., Mineola, L.I., N.Y. 11501

[21] Appl. No.: 910,252

[22] Filed: Sep. 19, 1986

Related U.S. Application Data

[63] Continuation of Ser. No. 538,347, Oct. 3, 1983, abandoned.

[51] Int. Cl.⁴ .............................................. A61B 17/11
[52] U.S. Cl. .................................... 128/334 R; 623/12
[58] Field of Search ............... 128/334 R, 334 C, 325, 128/DIG. 21; 604/8–10, 101, 282, 280; 623/11, 12, 1

[56] References Cited

U.S. PATENT DOCUMENTS

| | | | |
|---|---|---|---|
| 1,470,707 | 10/1923 | Bates | 128/334 R |
| 2,428,918 | 10/1947 | Miller | 128/334 R |
| 3,783,454 | 1/1974 | Sausse et al. | 3/1 |
| 3,818,511 | 6/1974 | Goldberg et al. | 3/1 |
| 4,134,405 | 1/1979 | Smit | 128/303 R |
| 4,182,339 | 1/1980 | Hardy | 128/334 R |
| 4,190,909 | 3/1980 | Ablaza | 128/334 R X |
| 4,225,979 | 10/1980 | Rey et al. | 3/1 |
| 4,313,231 | 2/1982 | Koyamada | 128/334 R X |
| 4,315,509 | 1/1982 | Smit | 128/303 R |
| 4,352,358 | 10/1982 | Angelchik | 128/334 R |
| 4,501,264 | 2/1985 | Rockey | 128/1 R |

FOREIGN PATENT DOCUMENTS

| | | | |
|---|---|---|---|
| 2834956 | 2/1980 | Fed. Rep. of Germany | 604/101 |
| 1526295 | 4/1968 | France | 3/1.4 |

OTHER PUBLICATIONS

Journal of Thoracic and Cardiovascular Surgery, pp. 1 and 49, vol. 54, No. 1, (7/1967), Belin et al.

Primary Examiner—Michael H. Thaler
Attorney, Agent, or Firm—Charles J. Knuth; Peter C. Richardson; Lawrence C. Akers

[57] ABSTRACT

The intestinal graft is a graft formed of a thin wall latex or silastic tube of various widths and lengths. The upper circular end of the tube and vertical seam are reinforced by fabric which contains a radiopaque filament. When the graft is joined to the submucosal layer of the bowel proximal to the usual anastomosis, it will prevent salivary esophago-gastrointestinal secretions, food, and fecal flow from coming in contact with the anastomotic closure site.

The graft will thus prevent leakage from any intestinal anastomosis and will guarantee a healed anastomosis by the time the graft is naturally expelled from rectum.

20 Claims, 20 Drawing Figures

INTRAINTESTINAL BYPASS TUBE

This is a continuation of application Ser. No. 538,347, filed on Oct. 3, 1983 now abandoned.

BACKGROUND OF THE INVENTION

The invention is in the field of surgery and particularly in the field of intestinal surgical procedures concerning resection, anastomosis, colostomy, esophagostomy, and the like.

The technique of surgical colostomy as a temporary solution to various colonic disorders has become an accepted and standard procedure for temporarily resolving the problems where a section of diseased colon must be removed for reasons such as diverticulitis, cancerous obstruction, perforation, trauma, etc. The technique of surgical cervical esophagotomy and tube gastrotomy are also accepted temporary procedures designed to protect esophageal anastomoses.

The major problem with intestinal anastomoses, especially those of the colon and esophagus are anastomotic dehiscences which are associated with high morbidity and mortality.

In the colon, the incidence of anastomotic dehiscences range from 5 to 69%, and at the turn of the century, it was associated with 30 to 50% mortality rate. This led to the development of fecal diversion procedures, colostomy, and ileostomy.

Recently, this proximal fecal diversion is being questioned. It is felt that it does not guarantee against anastomotic leaks and does not improve the morbidity of colonic surgery. The construction and subsequent closure of a colostomy is associated with a high morbidity and mortality which ranges from 0.5 to 57%, and to 0 to 34% respectively.

The mortality rate from colonic anastomosis leakage rises in patients with diverticulitis and low colonic resections. The mortality rate for emergency resection of the colon in the clinical setting reaches as high as 28%. Experimentally a 24% mortality rate has been reported in resection of simulated diverticulitis.

Esophageal dehiscences are associated with even higher morbidity and mortality. The perioperative mortality following esophageal surgery ranges from 6 to 57%. When associated with anastomotic leakage, these figures escalate from 50% to 100%.

Because of high esophageal leak rates, many structures have been used to reinforce the esophageal anastomosis. These include lung, visceral pleural patch, omentum, peritoneum, pericardium, intercostal pedicle, and gastric fundus. All these techniques have one thing in common; they lie external to the esophageal anastomosis and act as patches without preventing the secretions or food from coming in contact with the anastomosis. For this reason they have not been consistently reliable both experimentally and clinically.

Anastomotic technique, shock, peritoneal sepsis, inadequate bowel preparation, malnutrition, coagulopathy, technical difficulty, diabetes, steroid dependence, uremic abscess, fistula, peritonitis, fecal soiling, poor blood supply, distal obstruction, absence of serosa, advanced age, and tension factors which may compromise the healing of an intestinal anastomosis. A combination of some of the above factors should lead to a staging of the management by means of a colostomy rather than a primary resection and anastomosis. Colonic loading is particularly dangerous as a cause of anastomotic dehiscences.

As noted above, because of the high incidence of intestinal anastomosis to leak, the salivary esophago-gastrointestinal secretion, food and fecal flow are diverted by proximal clostomy, cecostomy, ileostomy, or cervical esophagotomy.

An intestinal anastomosis becomes leak proof only after it is completely sealed. The gastrointestinal tract heals much more rapidly than the skin. The tensile strength of the intestine is acquired earlier because the strength of a newly formed collagen reaches that of the old collagen more rapidly. A 10-to-12-day anastomosis has a very strong tensile strength because it is rigid and under less tension. The normal intestine can be shown to burst before disruption of the anastomosis.

In studies on dogs in connection with the present invention, the esophageal and colonic anastomosis were subjected to maximal stress. All dogs were fed on the first postoperative day, all dogs had no bowel preparation and had a maximal colonic load. Where gross dehiscences of the esophagus and colon were created, and a graft was not used, these animals died. In those where the implantation of the temporary intraintestinal graft was performed, there were no deaths. The graft has successfully prevented the esophageal and colonic anastomosis from leaking. It guarantees that the anastomoses and all the created gross dehiscences would procede to complete healing before the graft passed naturally in two to three weeks time. The graft becomes the innermost lining of the intestine and as such act as a protective barrier between the secretions, food or feces, and the intestinal mucosa. The implantation of the intraintestinal graft has been demonstrated to be a safe, uncomplicated procedure which completely protects an anastomosis even in the presence of gross dehiscence.

As a solution to the anastomotic leak rate and the considerable complication rate accompanying proximal colostomy or esophagostomy, the present invention provides an intraintestinal graft that diverts all the salivary esophago-gastointestinal secretion, food, and fecal flow from the proposed anastomotic site more safely and expeditiously than any other method and does so with one operation only. This tube then substitutes for a colostomy and esophagostomy and prevents leakage at the anastomosis. This invention is applicable for anastomoses of most intestinal and related human and animal fluid ducts where a complete diversion of fluids is needed.*

* See Exhibits A,B

SUMMARY OF THE INVENTION

The new invention is a technique and a device whereby leakage from an anastomosis and problems directly resulting from such leakage are eliminated. The invention is an intraintestinal bypass graft formed perferably of a soft latex or silastic tube with a radiopague axial line for X-ray observation after implantation. One end of the tube is sutured or stapled to the mucosal or submucosal linings, and after a period of about 10 to 15 days during which the anastomosis is healing, the bypass graft separates naturally from the wall of the intestine, and is finally expelled naturally from the anus. This temporary graft prevents leakage at the anastomosis and thus substitutes for and makes unnecessary a colostomy or any other diversionary procedure.

This bypass invention is applicable to reduce or prevent leakage of anastomosed body conduits of many types including colonic, intestinal, esophageal, etc. The diameter of the bypass graft will correspond to the bore of the excised conduit, and the length of the bypass will vary with the length of colon or other duct extending downstream from the anastomosis. A reinforcing collar is particularly important at the proximal or upstream end of the bypass, since that portion is sewn and must not tear, shrink or stretch even though it must remain generally flexible enough so as not to interfere with the peristaltic pressure and natural contractions of the excised conduit.

It is considered that this procedure, implantation of the intraintestinal graft, can replace and eliminate all the following complications, phychological and physical stress, odor, erratic function of the stoma, cost, nursing care, skin problems, infection, herniation, prolapse, perforation, risk of a major operation, and repeated hospitalization by creating and closing a temporary colostomy in a safe and expeditious manner. It is suggested that its use be considered whenever a colonic anastomosis and closure are at risk. This includes low anterior resection, perforated diverticulitis, and a combination of three or more factors known to be associated with anastomotic breakdown. Further it should end the debate concerning the management of the traumatic colon injuries and obviate a long and costly hospital stay when exteriorization is chosen. It should be used for all esophageal anastomoses and should be suitable for use in the perforated esophagus, both iatrogenic and spontaneous.

This procedure can prevent an anastomosis stricture that may occur with proximal colostomy because the anastomosis will be dilated by the feces inside the graft. It is also indicated that the latex graft may possibly prevent the implantation of disseminated intraluminal tumor cells at the suture line.

The intraintestinal graft together with an adequate blood supply to the tension-free anastomosis will provide optimum connditions for a healing and safe anastomosis.

BRIEF DESCRIPTION OF THE DRAWINGS

1. A fragmentary schematic view of a colon which has been excised and is prepared for attachment to the intraintestinal bypass graft (tube) of this invention prior to anastomosis. Eversion of cloth-covered end of graft and proximal colon are shown.

2. Posterior anastomosis of the graft to the everted bowel.

3. Complete anastomosis of the everted graft to the everted bowel.

4. Margin of unfolded graft anastomosed to the everted colon.

5. Proximal colon restored to normal appearance. Posterior colonic anastomosis completing the graft is seen tied to the rectal tube in distal colon.

6. Complete colonic and tubal anastomosis.

7. Initial stage of attachment of the bypass tube to the proximal colon with the EEA stapler device.

8. Purse string around submucosa at the colostomy site and insertion of EEA with graft tube in the proximal colon.

9. Approximation of submucosa to tube by the EEA.

10. Tubal anastomosis and posterior colon to colon anastomosis, performed with the graft tied to a rectal tube in the distal colon.

11. A complete tubal and colonic anastomosis.

12. A view of the graft as it lies in the rectal ampulla after its been anastomosed to the proximal colon.

13. Mobilization of the esophagus.

14. Eversion of the proximal esophagus by four stay sutures.

15. Posterior anastomosis of the graft to the proximal everted esophagus.

16. Complete anastomosis of the everted graft to the everted bowel.

17. Proximal esophagus restored to normal appearance.

18. Complete esophageal and graft anastomosis.

19. Complete esophagojejunal anastomosis with the implanted graft.

20. Complete esophagogastric anastomosis with the implanted graft.

Figure 1:
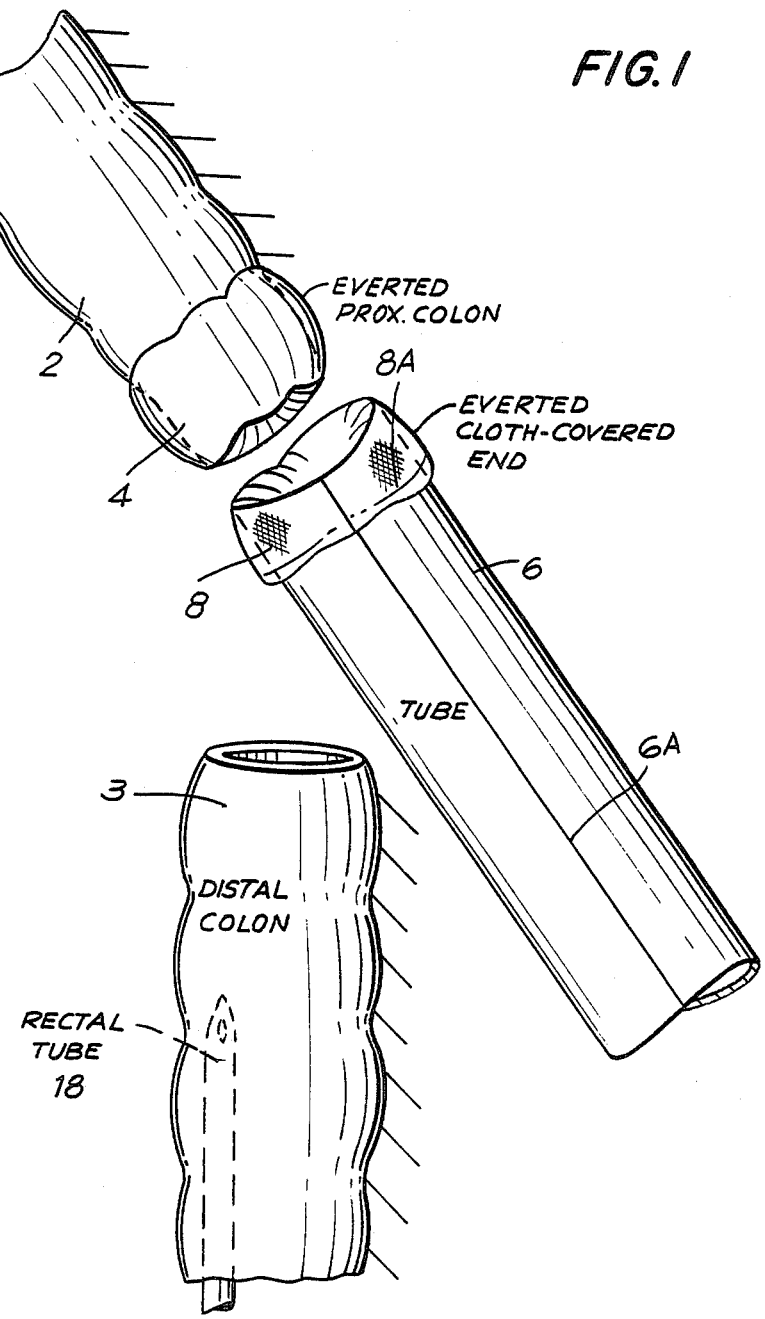
Figure 2:
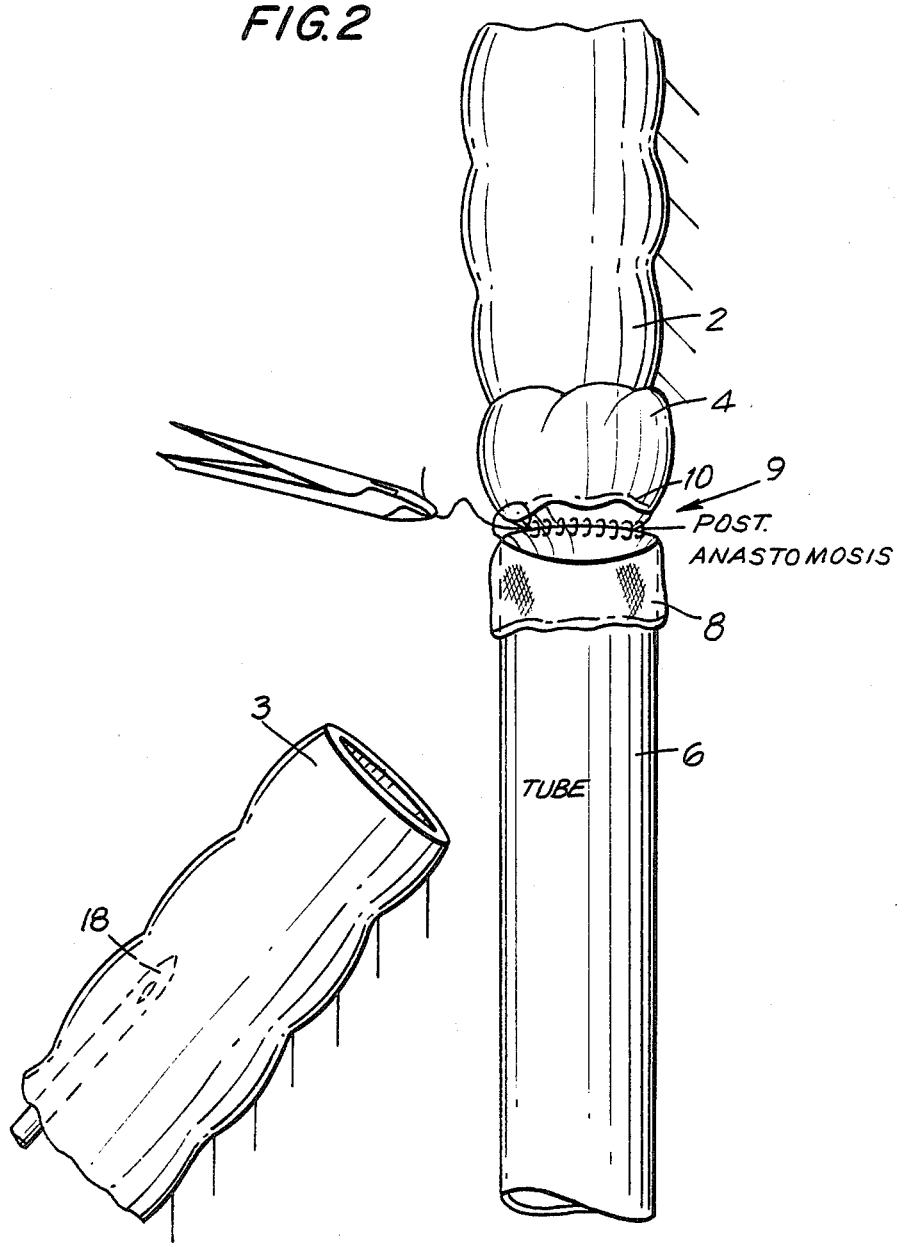
Figure 3:
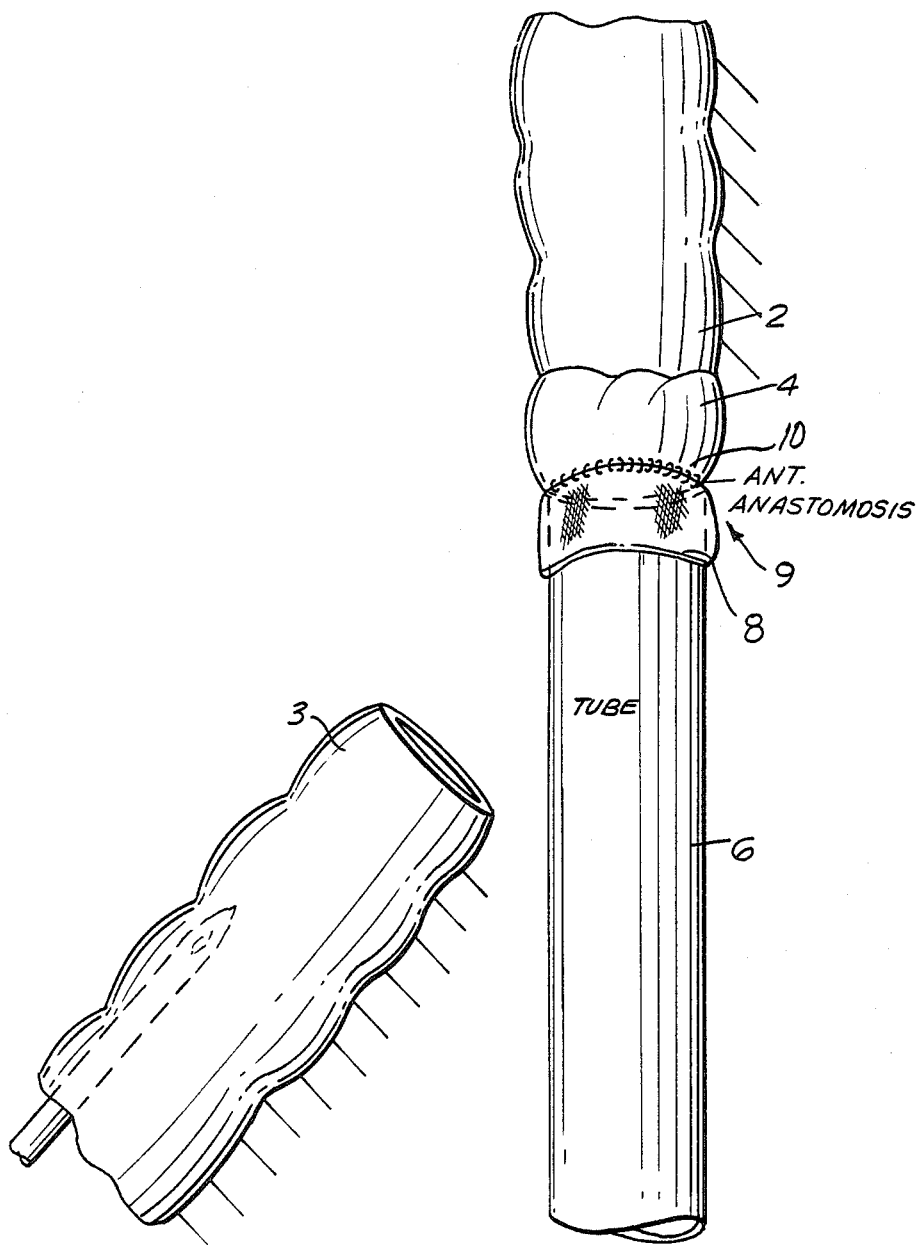
Figure 4:
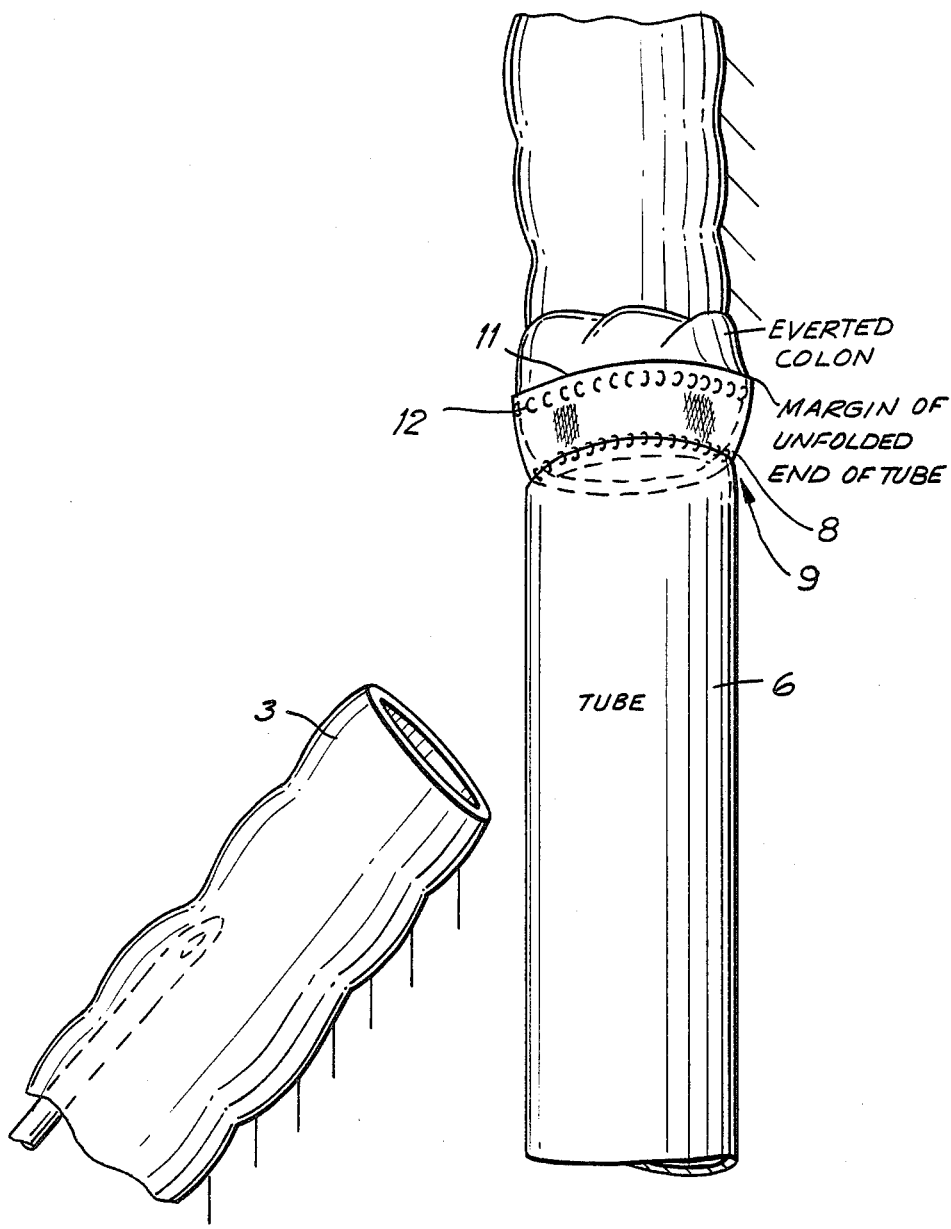

FIG. 1 shows the first stage of a typical colon segmental resection procedure. A section of colon is removed leaving the proximal colon 2 and distal colon 3 with a rectal tube or leader 18 for later use extending from the distal colon downward to and out the anus. The end 4 of the proximal 2 colon is everted by a length of about 5 cm. The new intracolonic bypass tube 6 has its proximal end 8 everted by a length of about 1 cm. and positioned adjacent and generally coaxially with proximal colon end 4. End 8 of the bypass tube 6 is cloth covered as indicated at 8A forming a circumferential reinforcing collar at that end. Along the length of tube 6 is radiopaque line 6A formed in a manner known in the prior art. As seen in FIGS. 2 and 3, proximal end 8 of the bypass tube is sutured or stapled 9 to the submucosa 10 of the proximal everted colon 4. The tube end 8 is then unfolded, as seen in FIG. 4, and the margin 11 of the tube 6 is again sutured at 12 to the mucosa 10.

Figure 5:
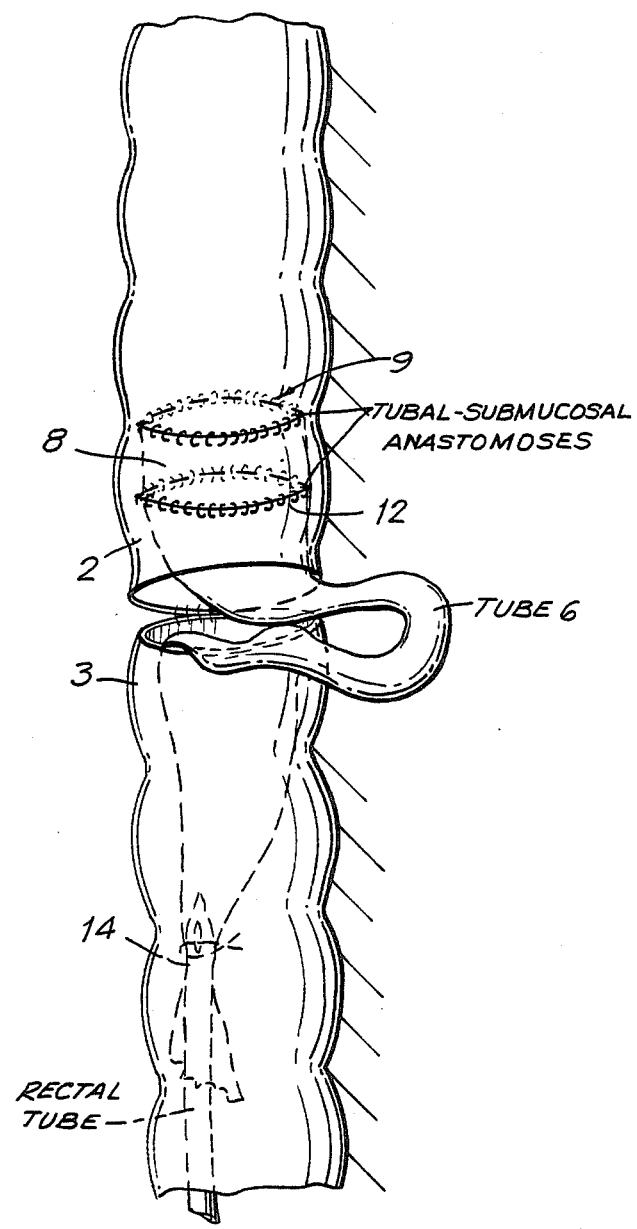
Figure 6:
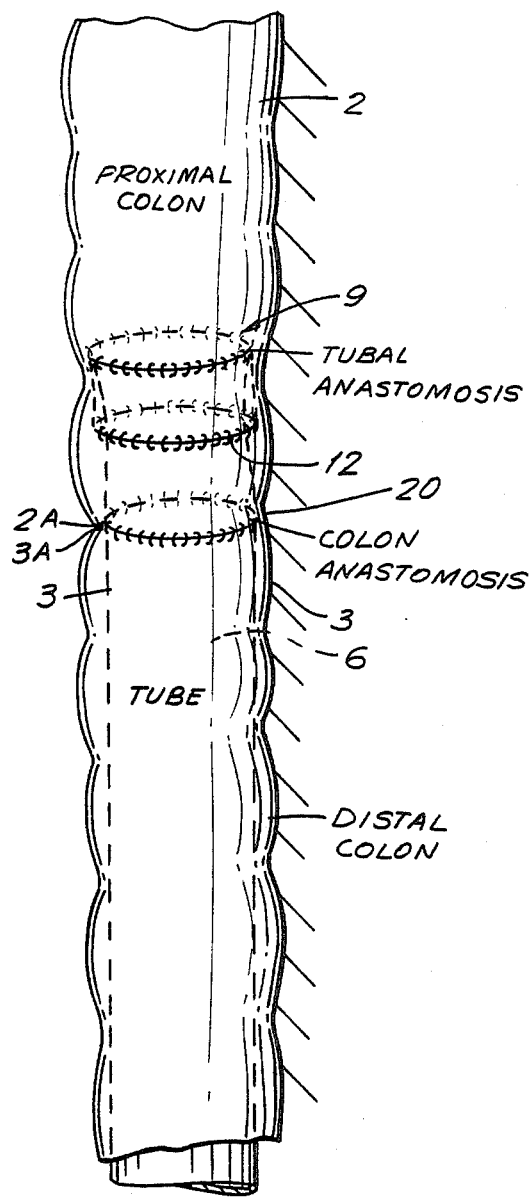

Next the proximal colon end 2 is un-everted as seen in FIG. 5, so that the proximal end 8 of the bypass tube 6 is within and enclosed by the proximal colon 2, with the remainder of the tube 6 hanging freely out of the proximal colon; the distal end 14 of the bypass tube is inserted into the distal colon 3 and secured to leader 18 therein and drawn downstream toward the anus. Lastly, as shown in FIG. 6 the proximal colon 2 has its terminal edge 2A anastomosed posteriorly by sutures 20 to the terminal edge 3A of distal colon 3. The distal end of the bypass tube is then tied to the rectal tube not shown and passed into the distal colon toward the anus. Typically the bypass tube extends two to ten inches beyond the anastomosis, depending on the location of same.

Figure 7:
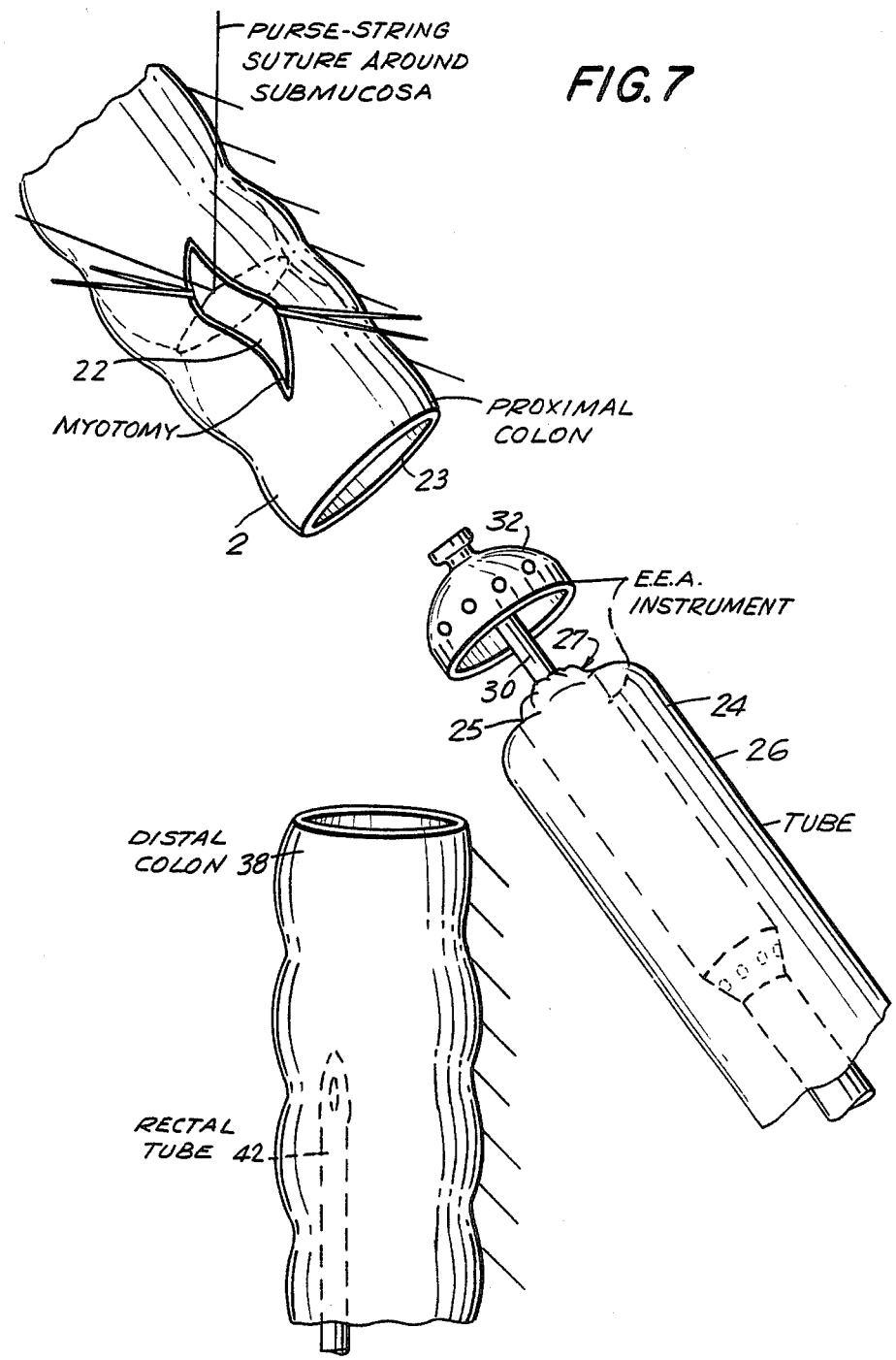
Figure 8:
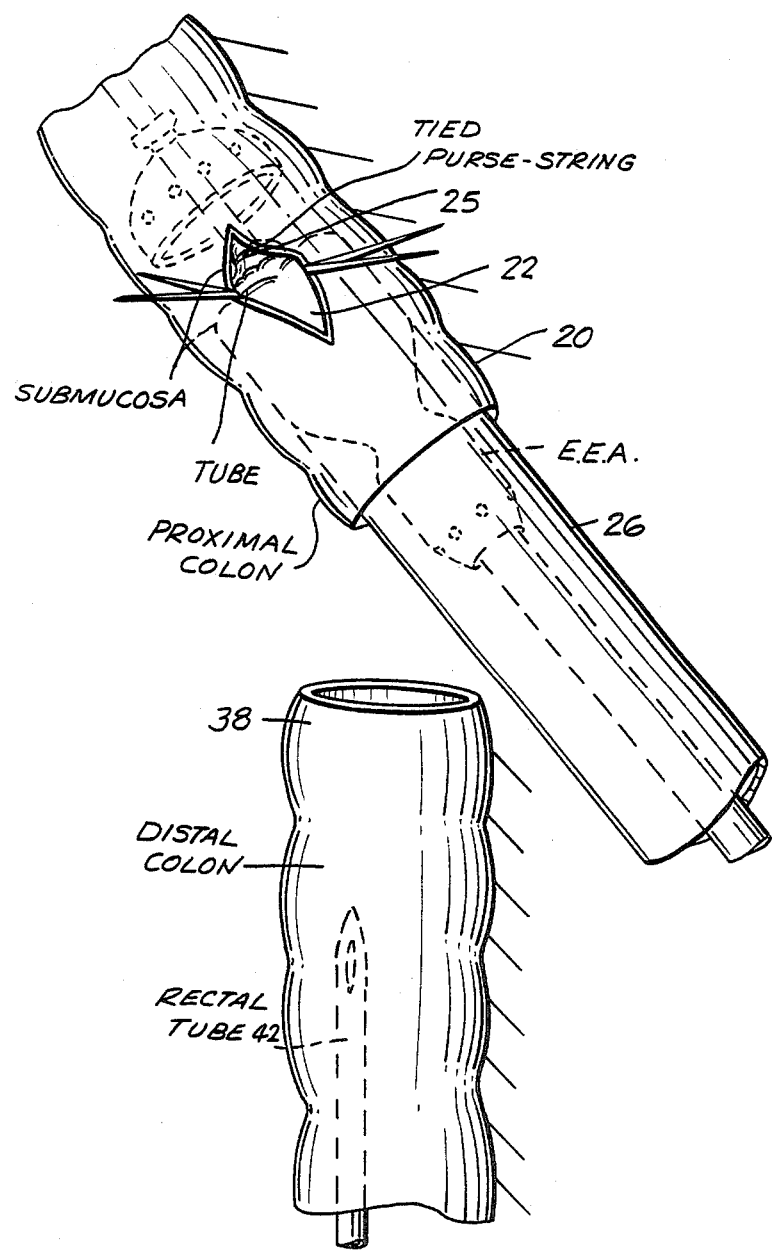
Figure 9:
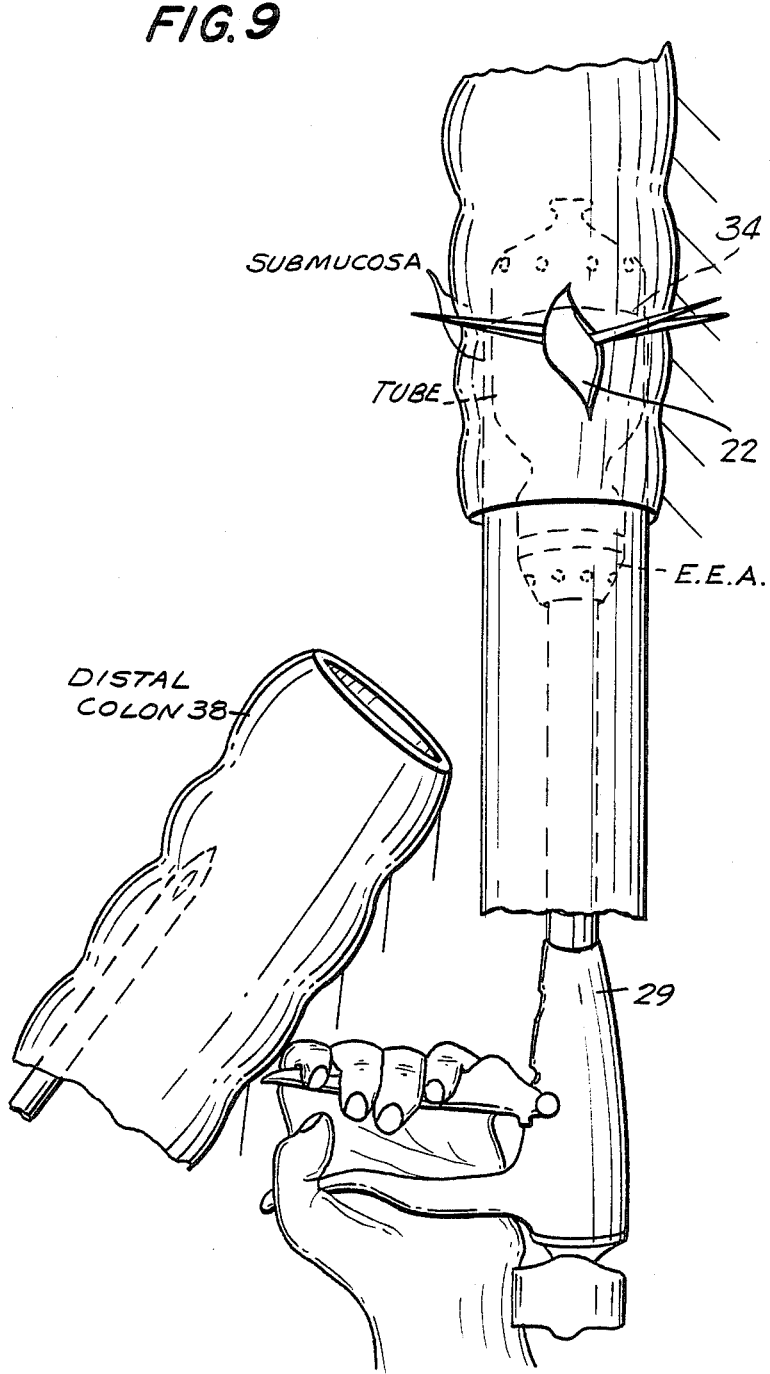
Figure 10:
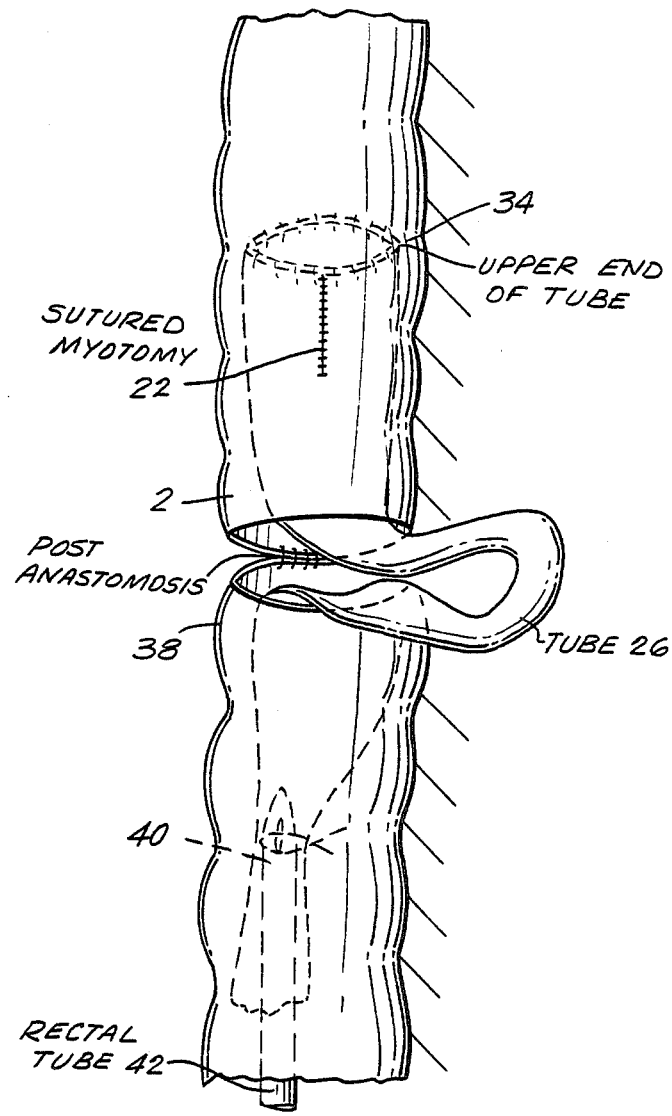
Figure 11:
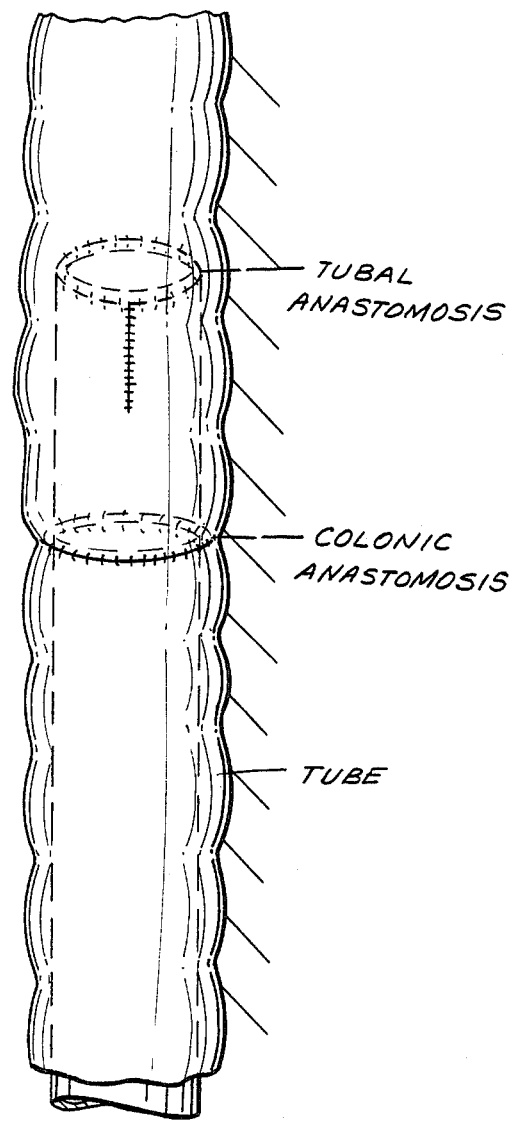
Figure 12:
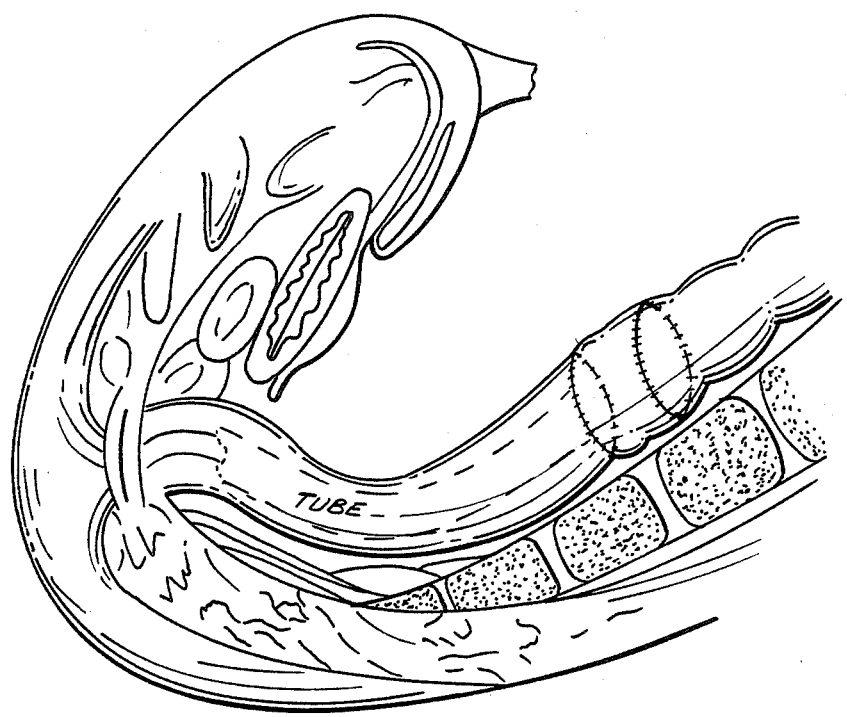
Figure 13:
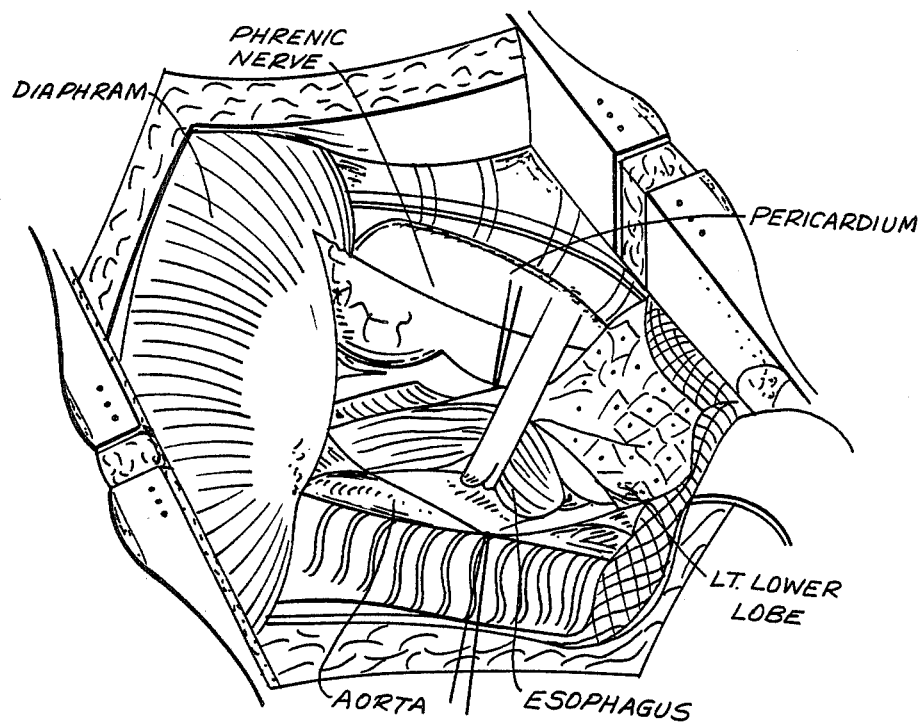
Figure 14:
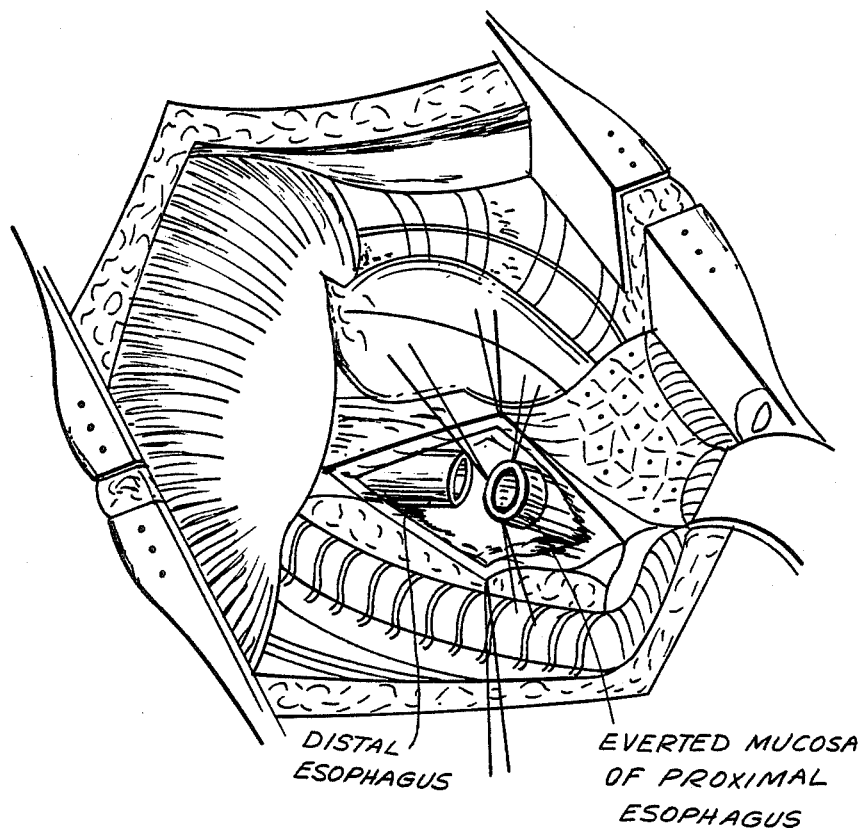
Figure 15:
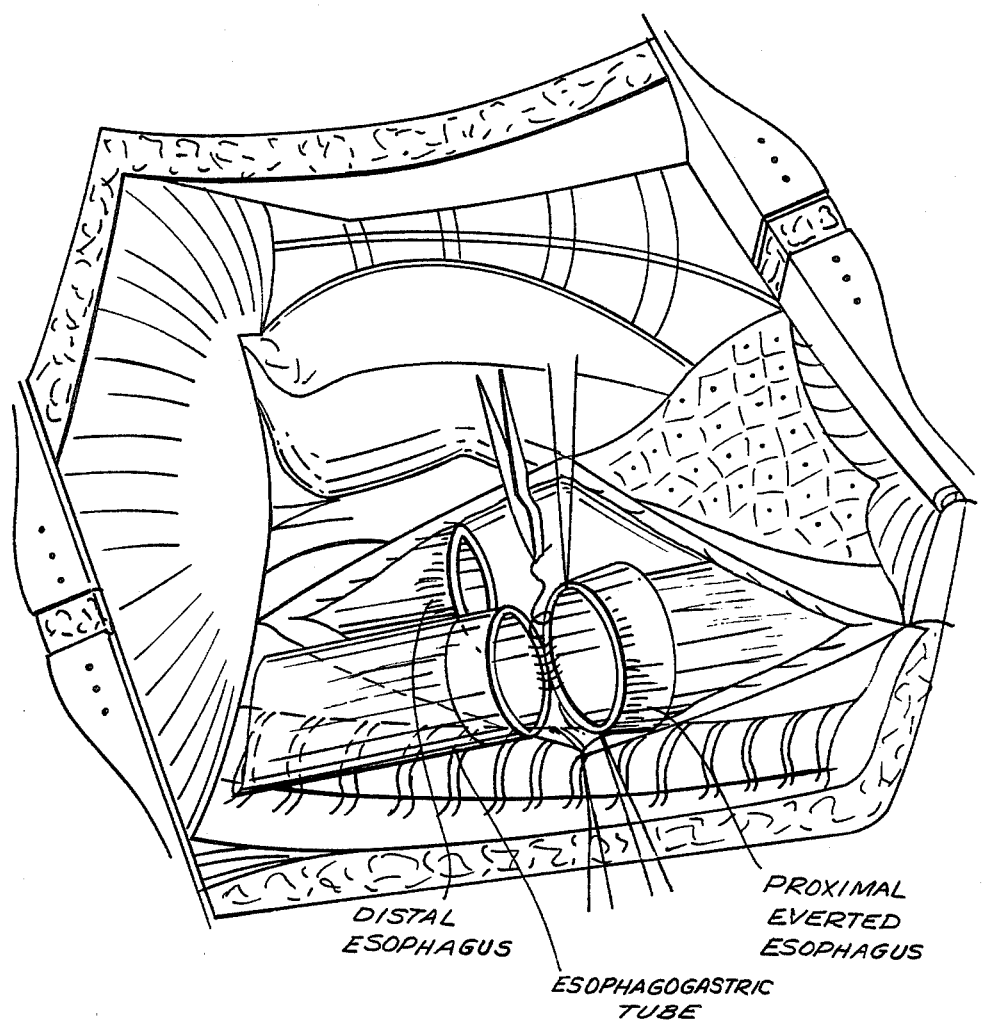
Figure 16:
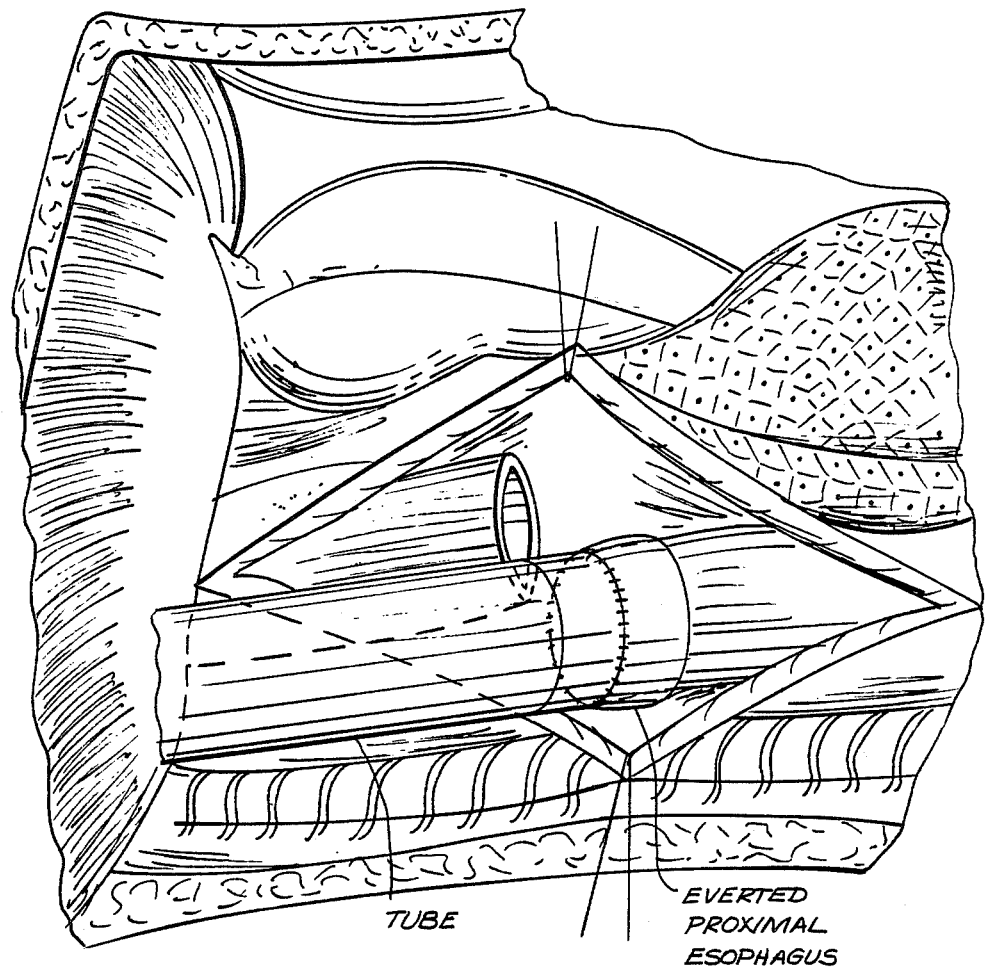
Figure 17:
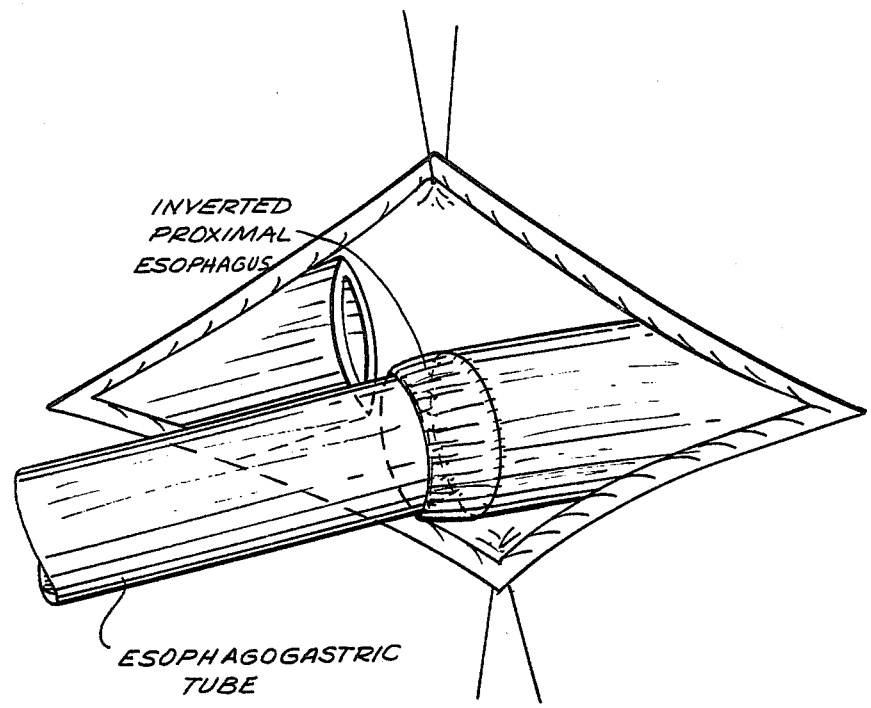
Figure 18:
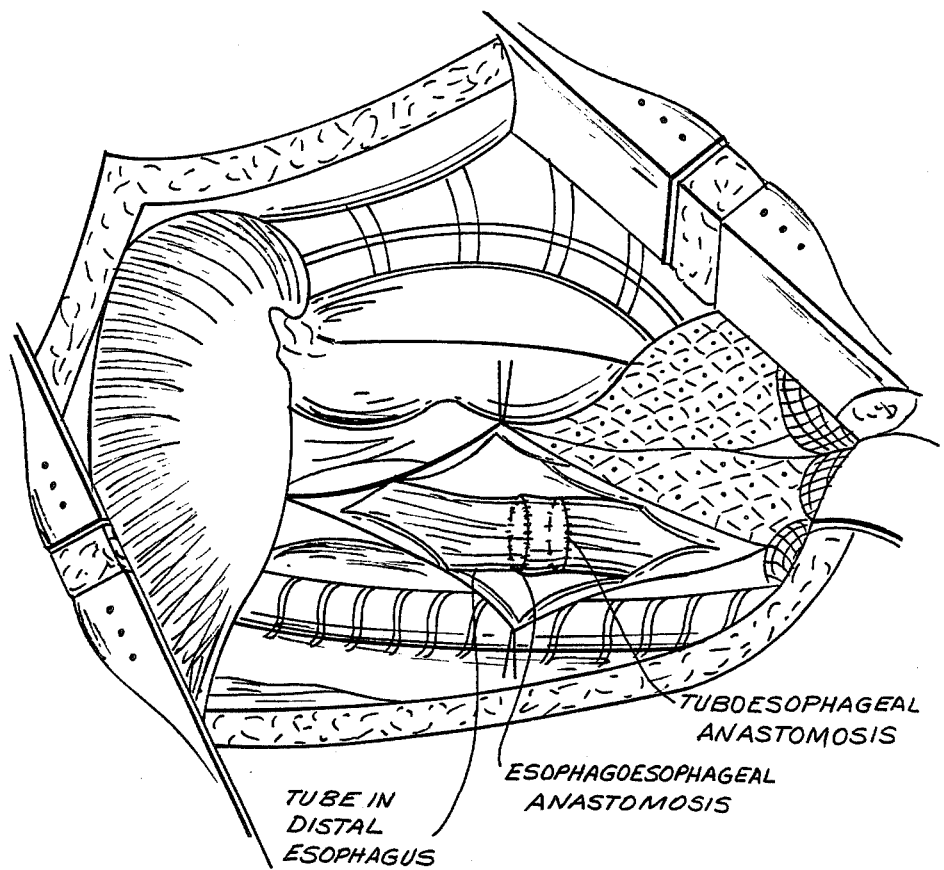
Figure 19:
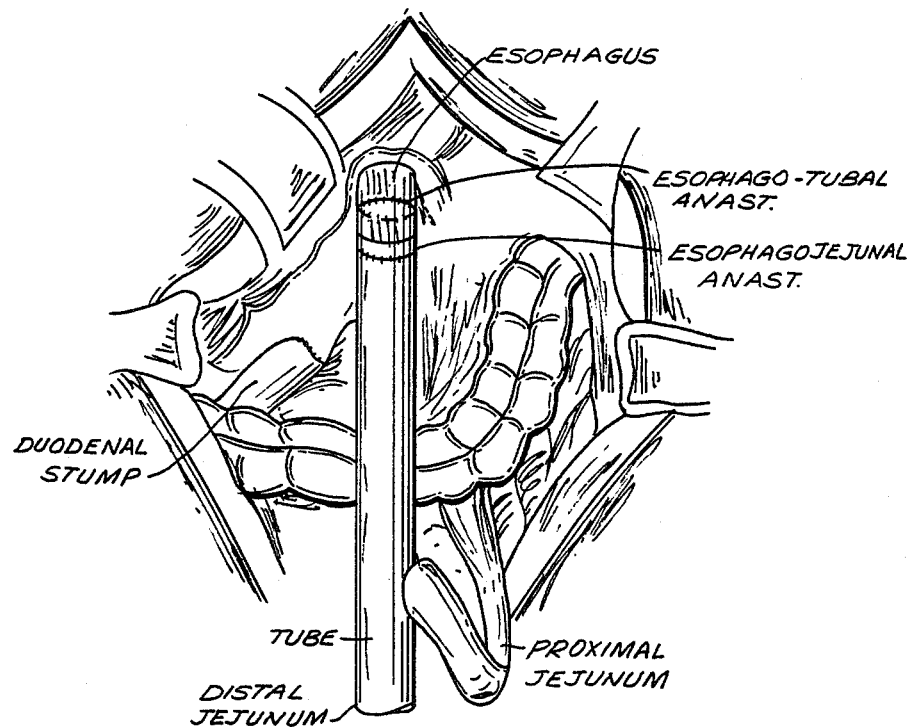
Figure 20:
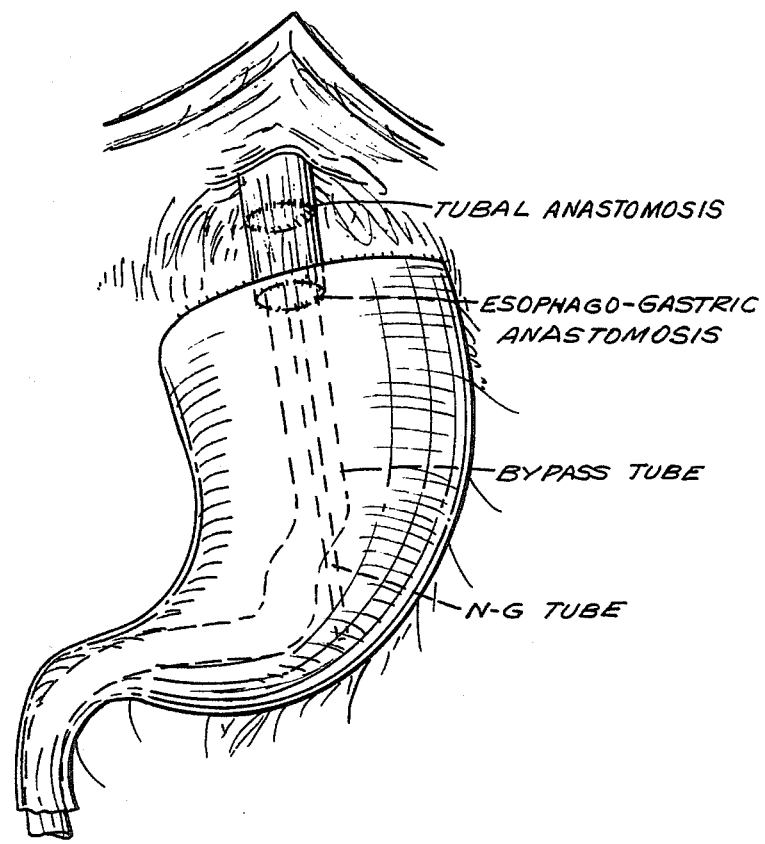

An alternative technique to suturing the intracolonic bypass as described above is to use more contemporary staples as illustrated in FIGS. 7–10. An incision 22 is made in the proximal colon slightly upstream of the terminal edge 23; the proximal end 24 of intracolonic bypass tube 26 receives a 28 of a surgical stapler 29 whose shank 30 extends out said end 24 and terminates in bell 32. As illustrated in FIGS. 7 and 8 the terminal edge 25 of the tube is drawn with purse string 27, and the bell 32 with the covered proximal end 24 of the tube is inserted into the proximal colon end until covered end 24 is directly adjacent the incision 22. Next, as seen in FIG. 9, the proximal colon is stapled about its circumference 34 to the bypass tube. Finally, incision 22 is closed as seen in FIGS. 9 and 10 and the remainder of tube 26 is inserted into the distal colon 38, the distal tube end 40 is secured to leader 42, and the proximal colon 2 is anastomosed to distal colon 38 as previously described.

The intracolonic bypass has been shown to be a safe uncomplicated procedure which temporarily completely diverts the fecal and colonic secretions from the anastomotic site. If 2/0 dexon is used to fix the tube, a 10 to 12 day anastomotic protection under the worst conditions is provided.

The morbidity and mortality in recent tests have been zero. It is believed that this procedure can replace and eliminate all the complications of creating and closing a temporary colostomy. The psychological and physical stress, odor, erratic function of the stoma, cost, nursing care, skin problems, infection, herniation, prolapse, perforation, risk of a major operation, and repeated hospitalization that accompany a colostomy can all be eliminated. The tubal bypass should eliminate anastomotic leaks with its morbidity and mortality. It is indicated that this procedure will prevent an anastomotic stricture that may occur with proximal colostomy, because the anastomosis will be dilated by the feces inside the tube. It is also indicated that the latex tube may possibly prevent the implantation of disseminated intraluminal tumor cells at the suture line. Intracolonic bypass together with an adequate blood supply to the tension-free anastomosis will provide optimum conditions for a healing and safe anastomosis.

Upon healing of the anastomosis the bypass tube is passed naturally from the anus by explusion. All tubes in recent tests were found with the intact sutures, indicating that the sutures separate from the bowel wall.

What I claim is:

1. A bypass graft suitable for attachment in the lumen of a resectioned intestine or duct upstream of the anastomosis thereof, the bypass graft consisting essentially of (1) a tube having opposite ends and formed along its entire length of a thin, water-impervious wall material having sufficient flexibility to conform to the natural movements of said intestine or duct surrounding it, and (2) freely collapsible reinforcing means extending circumferentially around at least one of said ends rendering said at least one end stronger than said thin wall material but still sufficiently flexible to conform to said natural movements, with said graft being freely collapsible and freely bendable throughout its entire length.

2. Apparatus according to claim 1 wherein said tube comprises latex.

3. Apparatus according to claim 1 wherein said material has thickness in the range of 0.005 to 0.050 mm.

4. Apparatus according to claim 1 wherein said material has thickness of approximately 0.01 mm.

5. Apparatus according to claim 1 wherein said reinforcing means comprises a cylindrical collar made of a woven fabric.

6. Apparatus according to claim 1 wherein said reinforcing means comprises a cylindrical collar formed as a thickened end portion of said tube.

7. A bypass graft of claim 1 further comprising a radiopaque means extending along the length of said tube and defining a line thereon.

8. A bypass graft suitable for attachment in the lumen of a re-sectioned intestine of a mammal upstream of the anastomosis of said intestine in order to protect said anastomosis and capable of being naturally expelled in an intact condition from the mammal's intestine through the mammal's anus without significant risk of injury, said bypass graft consisting essentially of (1) a non-perforated cylindrical tube having opposite ends and formed along its entire length of a thin water-impervious wall material having sufficient flexibility to conform to the natural movements of the intestine surrounding it, and (2) freely collapsible reinforcing means extending circumferentially around at least one of said ends of said cylindrical tube for rendering said at least one end stronger than said thin wall material but still sufficiently flexible to conform to said natural movements, with said graft being freely collapsible and freely bendable throughout its entire length.

9. A bypass graft according to claim 8 wherein said reinforcing means comprises a reinforcing collar.

10. A bypass graft according to claim 9 wherein said reinforcing collar comprises a cloth material sewn to said tube.

11. A bypass graft according to claim 9 wherein said reinforcing collar comprises a plurality of layers or folds of the wall material of said cylindrical tube of said bypass graft.

12. A bypass graft according to claim 8 wherein said reinforcing means comprises a reinforcing collar of cloth sewn to each end of said tube.

13. A bypass graft according to claim 8 wherein said tube is seamless along its length between its ends.

14. A bypass graft according to claim 7 wherein said tube comprises latex.

15. A bypass graft according to claim 7 wherein said tube comprises silastic.

16. A bypass graft according to claim 7 wherein said wall material has thickness in the range of 0.005 to 0.050 mm.

17. A bypass graft according to claim 7 wherein said wall material has thickness of approximately 0.01 mm.

18. A bypass graft according to claim 7 wherein said reinforcing means comprises a cylindrical collar made of a fabric.

19. A bypass graft according to claim 7 wherein said reinforcing means comprises a cylindrical collar formed as a thickened end portion of said tube.

20. A bypass graft of claim 8 further comprising a radiopaque means extending along the length of said tube and defining a line thereon.

* * * * *